United States Patent [19]

Bianchini et al.

[11] Patent Number: 4,535,639
[45] Date of Patent: Aug. 20, 1985

[54] VAPOR SPILL MONITORING METHOD

[75] Inventors: Gregory M. Bianchini; Thomas G. McRae, both of Livermore, Calif.

[73] Assignee: The United States of America as represented by the United States Department of Energy, Washington, D.C.

[21] Appl. No.: 507,188

[22] Filed: Jun. 23, 1983

[51] Int. Cl.³ .............................................. G01N 1/24
[52] U.S. Cl. .................................................. 73/863.11
[58] Field of Search ........................ 73/863.11, 863.12

[56] References Cited

U.S. PATENT DOCUMENTS

| | | | |
|---|---|---|---|
| 2,691,890 | 10/1954 | Moore | 73/863.11 |
| 2,731,832 | 1/1956 | Johnson | 73/863.11 |
| 3,107,535 | 10/1963 | Kraftson | 73/863.11 |
| 3,152,479 | 10/1964 | Small | 73/863.12 |
| 3,938,391 | 2/1976 | Winkler . | |
| 4,073,619 | 2/1978 | Lawson . | |
| 4,250,142 | 2/1981 | Kollmai . | |
| 4,262,522 | 4/1981 | Reich . | |

OTHER PUBLICATIONS

Koopman, R. P. et al.; Description and Analysis of Burro Series 40-m³L.N.G Spill Experiments, Aug. 14, 1981, Lawrence Livermore Lab.

Primary Examiner—S. Clement Swisher
Attorney, Agent, or Firm—Henry P. Sartorio; L. E. Carnahan; Judson R. Hightower

[57] ABSTRACT

Method for continuous sampling of liquified natural gas effluent from a spill pipe, vaporizing the cold liquified natural gas, and feeding the vaporized gas into an infrared detector to measure the gas composition. The apparatus utilizes a probe having an inner channel for receiving samples of liquified natural gas and a surrounding water jacket through which warm water is flowed to flash vaporize the liquified natural gas.

7 Claims, 2 Drawing Figures

VAPOR SPILL MONITORING METHOD

The U.S. Government has rights in this invention pursuant to Contract No. W-7405-ENG-48 between the U.S. Department of Energy and the University of California, for the operation of Lawrence Livermore National Laboratory.

BACKGROUND OF THE INVENTION

The invention relates to sampling a liquified gas for analytical purposes, and more particularly, to continuously taking a sample of a liquified gas, vaporizing the gas, and transferring the vaporized gas to a remote analyzer.

Natural gas is a combustible gas that occurs in porous rock of the earth's crust and is found with or near accumulations of crude oil. Natural gas is a mixture of hydrocarbon fuels, with methane ($CH_4$) the most common constituent, typically about 85 percent and often 90 percent or more. Ethane ($C_2H_6$) may be present in amounts typically from 2 to 10 percent, followed by propane ($C_3H_8$) typically 1–4 percent. Other constituents may also be present in trace amounts. The composition varies depending primarily on the original source and the storage history. The main use of natural gas is for fuel.

Since 600 cubic feet of natural gas condenses to less than 1 cubic foot of liquid, liquified natural gas (LNG) is a useful product of natural gas, particularly for storage purposes. However, because liquified natural gas has a low critical temperature, about $-100°$ F., is difficult to liquify and maintain in the liquid state. The temperature of LNG is typically about $-367°$ F. A variety of large insulated tanks have been designed for storage as well as special insulated tankers for ocean transport. The storage and transport of liquified natural gas create a possiblity of serious accidents.

The Lawrence Livermore National Laboratory has been conducting a series of tests at the Naval Weapons Center, China Lake, Calif. In these tests quantities of liquified natural gas from 5 to 40 cubic meters are spilled onto water which is much warmer than the cold LNG. The dispersion of the LNG vapor cloud in the atmosphere under various conditions and the combustion of the gas cloud are measured. In addition, the phenomenon of large and unexpected explosions known as rapid phase transformations (RPT) are being studied. The composition of the LNG varied from 94% $CH_4$, 5% $C_2H_6$, 1% $C_3H_8$, having the greatest percentage of methane, to 83% $CH_4$, 14% $C_2H_6$, 3% $C_3H_8$ having the highest percentage of non-methane constituents.

Because the composition of the LNG varies during the spill, it is desirable to obtain a continuous composition profile of the spill in order to study the dispersion, combustion and RPT explosions. The composition of the vapors can be measured by an IR gas detector; however, the detector cannot be placed near the spill point because it will be damaged or destroyed during the ensuing tests. Also, the LNG must be vaporized before entering the IR gas detector.

U.S. Pat. No. 3,938,391 to Winkler discloses a sampling device for liquified gases which includes a container for receiving a sample of the liquid and a communicating chamber in which the liquid is converted to a gas which is withdrawn through a valve for analysis.

U.S. Pat. Nos. 4,250,142 to Kollmai, 4,073,619 to Lawson, 4,262,522 to Reich and 4,138,891 to Graves, et al. relate generally to the detection or sampling of gases from sources including oil and gas wells and steel making vessels.

Accordingly, it is an object of the invention to provide continous sampling of liquified natural gas effluent from a spill pipe.

It is another object of the invention to continuously measure the composition of liquified natural gas flowing from a spill pipe.

It is a further object of the invention to continuously remove a sample of liquified natural gas, vaporize the liquified gas and transfer the vaporized gas to a remote IR detector.

It is also an object of the invention to provide real time LNG composition monitoring.

SUMMARY OF THE INVENTION

The invention is a method and apparatus for continually monitoring the composition of liquified natural gas flowing from a spill pipe during a spill test by continually removing a sample of the LNG by means of a probe, gasifying the LNG in the probe, and sending the vaporized LNG to a remote IR gas detector for analysis. The probe comprises three spaced concentric tubes surrounded by a water jacket which communicates with a flow channel defined between the inner and middle, and middle and outer tubes. The inner tube is connected to a pump for providing suction, and the probe is positioned in the LNG flow below the spill pipe with the tip oriented partly downward so that LNG is continuously drawn into the inner tube through a small orofice. The probe is made of a high thermal conductivity metal. Hot water is flowed through the water jacket and through the flow channel between the three tubes to provide the necessary heat transfer to flash vaporize the LNG passing through the inner channel of the probe. The gasified LNG is transported through a connected hose or tubing extending from the probe to a remote IR sensor which measures the gas composition.

DETAILED DESCRIPTION OF THE PREFERRED EMBODIMENTS

Figure 1:
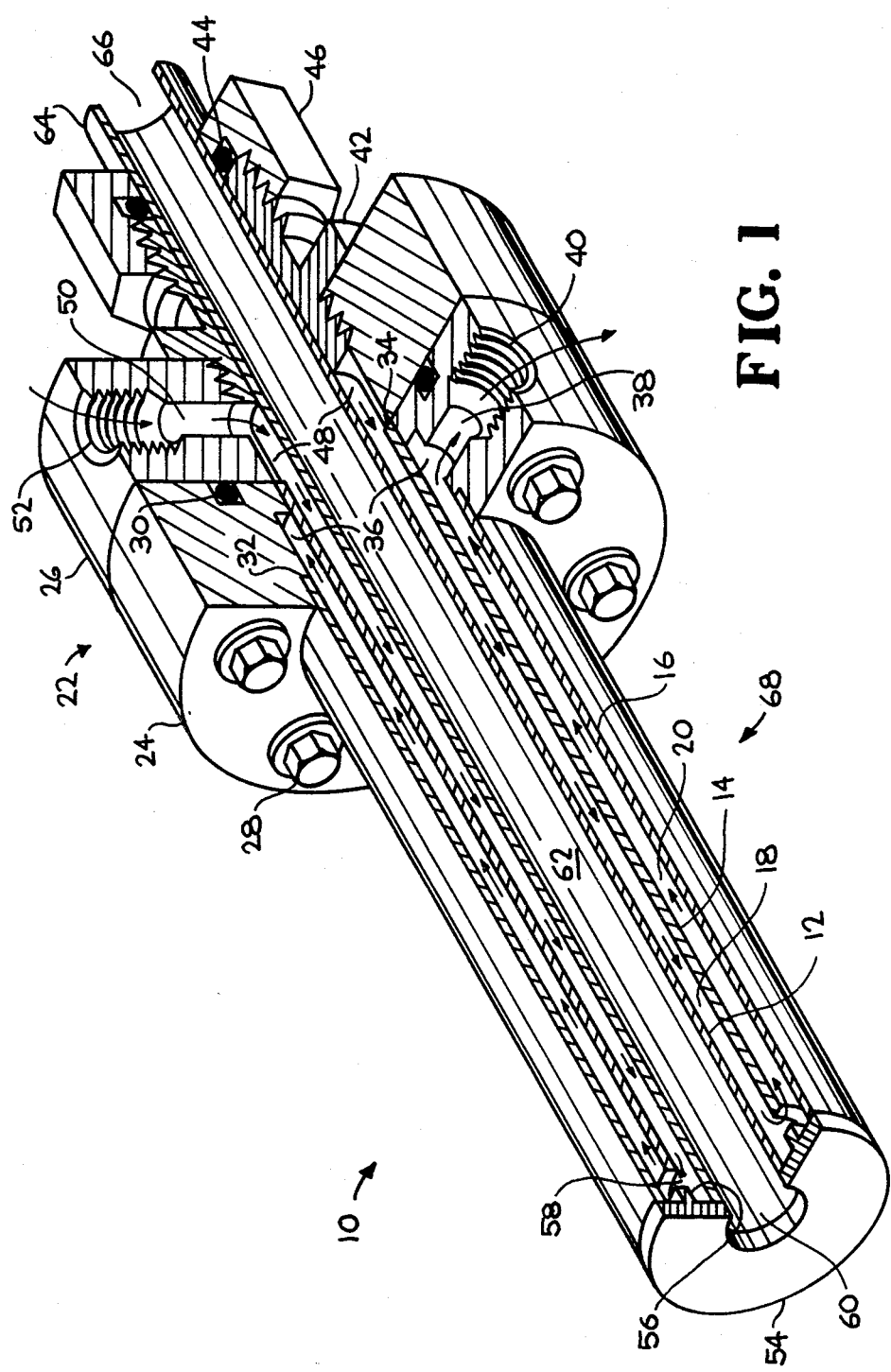
FIG. 1 shows a sectional view of the probe for continuously removing and vaporizing LNG samples.

The probe 10, as illustrated in FIG. 1, comprises three spaced concentric tubes 12, 14, 16. The inside tube 12 and the center tube 14 define therebetween an annular channel 18, and the center tube 14 defines with the outer tube 16 and annular channel 20. A manifold 22 made up of two halves, an outlet manifold 24 and an inlet manifold 26 which have sealing O-ring 30 therebetween and are bolted together with bolts 28, is attached to the tubes 12, 14, 16.

The top of outlet manifold 24 is attached to the end 32 of outer tube 16, which is the shortest tube, for example by hard solder. The bottom of the outlet manifold 24 is attached to the end 34 of center tube 14 which extends beyond the end 32 of outer tube 16. The attachment of the tubes 16 and 14 to the outlet manifold 24 at the ends 32 and 34 of the tubes, respectively, holds the tubes 16 and 14 in a fixed spaced relationship defining the channel 20 therebetween. The outlet manifold 24 defines an annular chamber 36 around the middle tube 14 beyond the end 32 of outer tube 16. The chamber 36 communicates with the channel 20, and outlet passage 38 extends through the outlet manifold 24 to the chamber 36. The outlet passage 38 may have treads 40 for attaching tubing.

The inlet manifold 26 is securely attached to outlet manifold 24 and surrounds the inside tube 12 beyond the end 34 of the middle tube 14. The tube 12 is the longest tube and extends the entire length of the probe. A fitting 42 tightly fits around the tube 12 and is attached to the bottom of the inlet manifold 26, e.g., by welding. The sealing O-ring 44 is held between the end of the fitting 42 and tube 12 by retaining nut 46, thereby providing a tight seal. The inlet manifold 26 defines an annular chamber 48 around inside tube 12 beyond the end 34 of the center tube 14. The fitting 42 and sealing O-ring 44 seal the chamber 48 at the bottom. The chamber 48 communicates with the channel 18 between tubes 12 and 14. An inlet passage 50 extends through the inlet manifold 26 to the chamber 48. The passage may have treads 52 for attaching tubing.

A probe tip 54 having a small opening 60 in the center is attached, e.g., by hard soldering, to the ends of inside tube 12 and outer tube 16 holding the tubes 12 and 16 in a fixed spaced relationship. The center tube 14 is recessed from the ends of tubes 12 and 16, and an annular projection 56 of tip 54 extends between and is attached to the ends of tubes 12 and 16 and defines with the end of tube 14 an annular space 58 which communicates with the channels 18 and 20 defined by the inner tube 12 and outer tube 16 with center tube 14, respectively. Accordingly, a continuous flow channel 68 extends along the length of the probe 10 above the manifold 22 from outlet manifold chamber 36 through channel 20 through space 58 through channel 20 to inlet manifold chamber 48. The opening 60 in the tip 54 allows LNG to enter the inner channel 62 of the probe 10.

Hot water is flowed into the inlet manifold 26 through inlet passage 50 and flows through channels 18, 20 to outlet manifold 24 and out through outlet passage 38. The tubes 12, 14 and 16 of the probe 10 are made of a high thermal conductivity metal, for example, OFHC copper. The water is flowed through the probe at a sufficient flow rate to provide the necessary heat transfer to flash vaporize the LNG passing through the inner channel 62 of the probe 10. By flowing the warm incoming water near the inner tube, maximum heat transfer to the LNG results. The gasified LNG then passes through the inner channel 62 to outlet 66 in end 64 to which gas removal means are attached.

A preferred embodiment of the probe is 12 inches long from tip to outlet end with a tip to manifold length of 9 inches. The probe is made of three OFHC copper tubes in a concentric orientation forming two approximately 0.010-inch annuluses between the tubes in which the water flows. The inner tube has an outer diameter of slightly less than ⅜ inch and a wall thickness of about 0.04 inch. The wall thicknesses of the middle and outer tubes are about 0.03 inch and 0.05 inch, respectively. The manifold is block-shaped, or alternatively cylindrical, and made of stainless steel. A ⅜ inch swagelok fitting is attached to the outlet manifold and fits around the inner tube.

Figure 2:
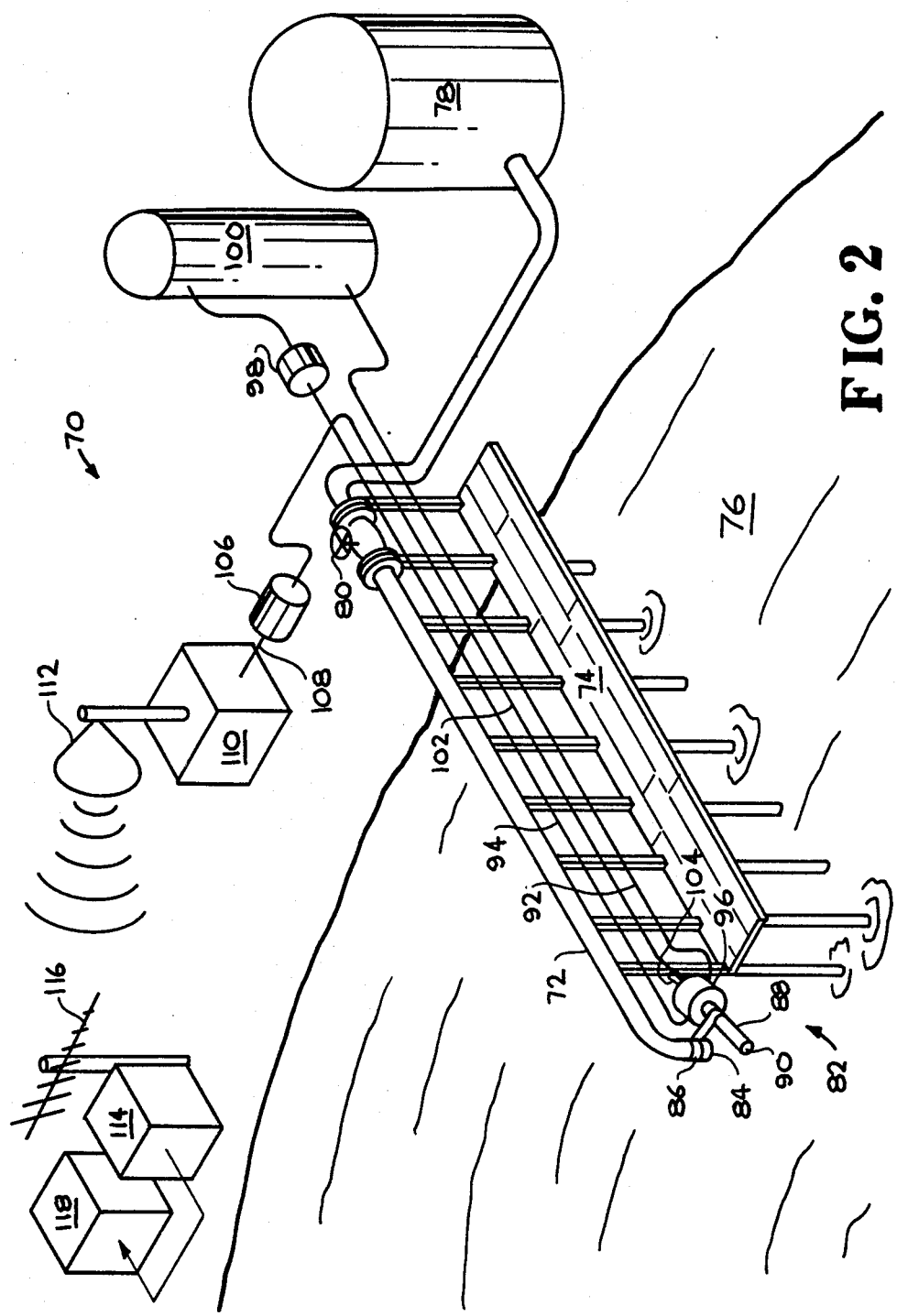
FIG. 2 is a schematic diagram of the LNG sampling and analysis system for continually monitoring LNG composition from a spill pipe.

An LNG monitoring system 70 for continuously monitoring the composition of LNG in a spill test is illustrated in FIG. 2. A spill pipe 72 is mounted on a support structure 74 over a pond 76. The spill pipe 72 is connected to a source 78 of liquified natural gas and has a valve 80 for regulating flow. A probe 82 is mounted to the spill 72 below the opening 84 by means of mounting bracket 86. The tube 88 extends into the flowing LNG and is oriented with the tip 90 in a partly downward direction. If the probe tip 90 faces upward, too much LNG enters the probe 82 and saturates the system. Water lines 92 and 94 are connected to the probe manifold 96, one line carrying hot water to the inlet manifold and the other removing water from the outlet manifold. The water lines 92 and 94 are connected by a pump 98 to a source 100 of hot water.

Tubing 102 is connected to the outlet end 104 of probe 82 and connected to a pump 106 to provide suction which draws a sample of liquified natural gas into the probe 82 through tip 90 where it is flash vaporized by the hot water flowing through the probe tube 88. The vaporized LNG is drawn by pump 106 through line 102 and pumped through line 108 to a conventional infrared gas detector 110. The IR detector 110 has a transmitter which transmits the data by means of transmitting antenna 112 to a receiver 114 with receiving antenna 116. The data signals go from receiver 114 to a data reduction device 118 for further analysis. The IR detector can accordingly be placed far from the spill pipe 72 so that it will not be damaged during the tests. The receiver and data reduction device can be located anywhere within the transmitting range of the IR detector 110.

In an illustrative embodiment of the LNG monitoring system a 10-inch spill pipe is positioned at the center of a 60-meter diameter pond. Up to 40 cubic meters of LNG are spilled during a test. The probe is positioned 10 to 12 inches below the spill pipe. High pressure hose, e.g. 2000 psi hose, wrapped in asbestos tubing for protection, is connected from the probe to the water pump. The pump pressure is typically 250–350 psi to flow hot water, typically at 90° F. or higher, through the probe at sufficient rates so that the LNG is vaporized, e.g., one gallon per minute plus flow rates. The probe output is connected to the vaccum end of a metal bellows pump by insulated 150 psi hose; with the exhaust of the metal bellows pump being connected to the IR detector intake. The pump is 175–200 feet away. From the pump to the detector ordinary 150 psi hose can be utilized. The IR detector is an Anarad gas detector.

Changes and modifications in the specifically described embodiments can be carried out without departing from the scope of the invention which is intended to be limited only by the scope of the appended claims.

We claim:

1. Method for continuous monitoring of LNG composition from a spill pipe comprising:

positioning the tip of a probe having three concentric spaced tubes in a generally downward orientation in a flow of LNG;

applying suction on the opposite end of the inside tube to draw a quantity of LNG into the inner tube;

flowing hot water in through the annular channel between the inner and middle tubes, and out through the annular channel between the middle and outer tubes, to provide heat transfer to vaporize the LNG;

transporting the vaporized LNG gas to a remote analyzer for determining the composition of the LNG.

2. The method of claim 1 wherein the water is flowed through at a rate sufficient to flash vaporize all the LNG drawn in by applying suction to the probe tube.

3. The method of claim 2 wherein the water has been preheated to a temperature of at least 90° F.

4. The method of claim 1 wherein water is flowed through the probe channels by pumping hot water from a hot water source through connecting lines to the probe.

5. The method of claim 1 wherein suction is applied to the inner tube of the probe by connecting the end of the tube to the vacuum side of a bellows pump.

6. The method of claim 5 wherein the vaporized LNG gas is transported to an analyzer by connecting the analyzer to the exhaust side of the bellows pump.

7. The method of claim 1 wherein the remote analyzer is an infrared detector.

* * * * *